United States Patent [19]

Farkas et al.

[11] 3,963,735

[45] June 15, 1976

[54] ACYLATED 2-AMINOTHIAZOLE DERIVATIVES

[75] Inventors: Lajos Farkas; Endre Kasztreiner; Ferenc Andrási; József Borsi; Istvan Elekes; Istvàn Polgàri, all of Budapest, Hungary

[73] Assignee: Egyt Gyogyszervegyeszeti Gyar, Budapest, Hungary

[22] Filed: Oct. 29, 1974

[21] Appl. No.: 518,732

[30] Foreign Application Priority Data

Nov. 9, 1973 Hungary............................. GO 1250

[52] U.S. Cl. ................. 260/294.8 D; 260/247.1 M; 260/268 H; 260/293.68; 424/248; 424/250; 424/263; 424/270
[51] Int. Cl.². .................................... C07D 213/56
[58] Field of Search ............................ 260/294.8 D

[56] References Cited
UNITED STATES PATENTS

| | | | |
|---|---|---|---|
| 3,705,153 | 12/1972 | Kaneko et al. .................... | 260/240 D |
| 3,806,512 | 4/1974 | Nakanishi et al. ............ | 260/294.8 D |

*Primary Examiner*—Alan L. Rotman
*Attorney, Agent, or Firm*—Young & Thompson

[57] ABSTRACT

New acylated 2-aminothiazole derivatives of the general formula (I),

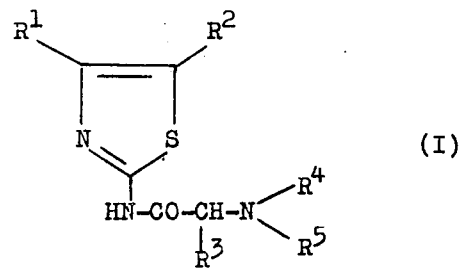

(I)

wherein
$R^1$ stands for phenyl group or a pyridyl group,
$R^2$ stands for hydrogen or lower alkyl,
$R^3$ stands for hydrogen, a lower alkyl group or benzyl group, and
$R^4$ and $R^5$ each represent hydrogen, a $C_{1-8}$ alkyl group, allyl group, a hydroxyalkyl group, a $C_{3-6}$ cycloalkyl group, β-dimethylaminoethyl group, β-diethylaminoethyl group, benzyl group, 2-furylmethyl group, or a phenyl group having optionally a halogen, methyl, methoxy or trifluoromethyl substituent, or
$R^4$ and $R^5$ may form, together with the adjacent nitrogen atom, a 5 to 8 membered polymethyleneimino group, morpholino group, piperazino group, N-methylpiperazino group or N-phenylpiperazino group, the compounds of formula I are anticholinergics.

2 Claims, No Drawings

ACYLATED 2-AMINOTHIAZOLE DERIVATIVES

This invention relates to new acylated 2-aminothiazole derivatives.

It has been found that new compounds possessing valuable pharmaceutical effects can be obtained by acylating the amino group of 2-aminothiazole with a derivative of an amino acid, e.g. glycine, alanine, phenylalanine, etc., and introducing a phenyl or pyridyl group into position 4, as well as a lower alkyl group into position 5 of the thiazole ring.

Accordingly, the invention relates to new acylated 2-aminothiazole derivatives having the general formula (I) and pharmaceutically acceptable acid addition salts thereof,

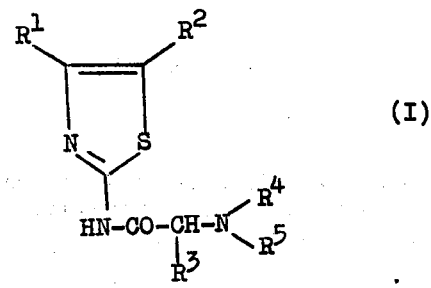

wherein
$R^1$ stands for phenyl group or a pyridyl group,
$R^2$ stands for hydrogen or a lower alkyl group,
$R^3$ stands for hydrogen, a lower alkyl group or benzyl group, and
$R^4$ and $R^5$ each represent hydrogen, a $C_{1-8}$ alkyl group, allyl group, a hydroxyalkyl group, a $C_{3-6}$ cycloalkyl group, $\beta$-dimethylaminoethyl group, $\beta$-diethylamioethyl group, benzyl group, 2-furylmethyl group, or a phenyl group having optionally a halogen, methyl, methoxy or trifluoromethyl substituent, or
$R^4$ and $R^5$ may form, together with the adjacent nitrogen atom, a 5 to 8 membered polymethyleneimino group, morpholino group, piperazino group, N-methylpiperazino group or N-phenylpiperazino group.

Processes for the preparation of compounds of the general formula (I) or acid addition salts thereof may comprise any of the following:

a. a thiazole derivative of the general formula (II),

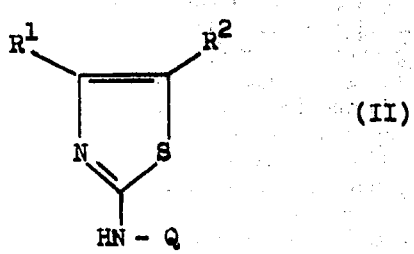

wherein $R^1$ and $R^2$ each have the same meanings as defined above, and Q stands for a group of the general formula X-CH($R^3$)-CO-, wherein $R^3$ has the same meanings as defined above and X stands for halogen, is reacted with an amine of the general formula (III),

wherein $R^4$ and $R^5$ each have the same meanings as defined above and Y stands for hydrogen, or b. a thiazole derivative of the general formula (II), wherein $R^1$ and $R^2$ each have the same meanings as defined above and Q stands for hydrogen, is reacted with an amine of the general formula (III), wherein $R^4$ and $R^5$ each have the same meanings as defined above, and Y stands for a group of the general formula Z-CO-CH($R^3$)—, wherein $R^3$ has the same meanings as defined above and Z represents halogen, a $C_{1-4}$ alkoxy group or an azido group, or c. haloketone of the general formula (IV),

wherein $R^1$, $R^2$ and X each have the same meanings as defined above, is reacted with an aminoacyl-thiourea of the general formula (V),

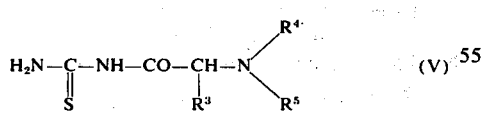

wherein $R^3$, $R^4$ and $R^5$ each have the same meanings as defined above.

The new compounds of the general formula (I) and their pharmaceutically acceptable acid addition salts possess valuable pharmacological properties, and can be applied primarily for the inhibition of the gastric hypersecretion as well as for the prophylaxis or treatment of gastric ulcer.

a. a thiazole derivative of the general formula (II),

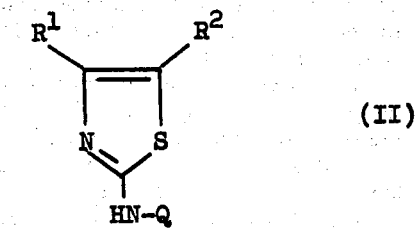

wherein $R^1$ and $R^2$ each have the same meanings as defined above, and Q stands for a group of the general formula X-CH($R^3$)-CO-, wherein $R^3$ has the same meanings as defined above and X stands for halogen, is reacted with an amine of the general formula (III),

wherein R⁴ and R⁵ each have the same meanings as defined above and Y stands for hydrogen, or b. a thiazole derivative of the general formula (II), wherein R¹ and R² each have the same meanings as defined above and Q stands for hydrogen, is reacted with an amine of the general formula (III), wherein R⁴ and R⁵ each have the same meanings as defined above, and Y stands for a group of the general formula Z-CO-CH(R³)-, wherein R³ has the same meanings as defined above and Z represents halogen, a $C_{1-4}$ alkoxy group or an azido group, or c. a haloketone of the general formula (IV),

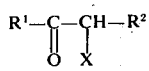

(IV)

wherein $R^1$, $R^2$ and X each have the same meanings as defined above, is reacted with an aminoacyl-thiourea of the general formula (V),

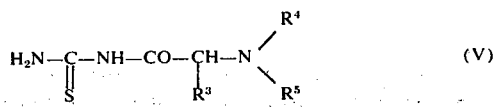

(V)

wherein $R^3$, $R^4$ and $R^5$ each have the same meanings as defined above, and, if desired, a free base of the general formula (I) is converted into its pharmaceutically acceptable acid addition salt, or a salt is converted into the free base.

The above reactions are performed preferably in the presence of an inert solvent or diluent. As solvent or diluent preferably water, lower alcohols, such as methanol, ethanol or isomeric propanols, ketones, such as acetone or butanone, ether-type solvents, such as diethyl ether, diisopropyl ether or di-n-butyl ether, tetrahydrofuran, dioxane, ethyleneglycol dimethylether, acid amide type solvents, such as formamide, methylformamide, dimethylformamide, N-methyl-acetamide, N-methyl-2-pyrrolidone, hexamethylphosphoric acid triamide, furthermore dimethylsulfoxide or a mixture of such solvents can be used.

The most preferred solvents for process variant a) are the lower alcohols and dimethylformamide, while the most preferred solvents for process variant c) are water and lower alcohols.

The process variants are performed preferably at temperatures ranging from −20°C to +150°C. When preparing the end-products according to process variant a) it is preferred, however, to apply temperatures lower than +80°C, since the 2-haloacyl-thiazole reactants are liable to enter into side reactions at higher temperatures. Such side reactions involve e.g. a ring closure with the nitrogen atom of the thiazole nucleus, or a quaternarization for compounds containing a pyridine ring.

Depending on the method of preparation and on the amount of reagents used, the compounds of the general formula (I) are formed either as free bases or as acid addition salts. Process variant a) yields either a free base or a hydrohalide, depending on the amount of the amine of the general formula (III). In process variant b) generally free bases, while in process variant c) generally hydrohalides are formed.

If a free base of the general formula (I) is to be prepared, one may proceed by adding a basic substance to the reaction mixture, and separating the obtained free base by known procedures. Alternatively, e.g. in the case of process variant c), one may also separate first the obtained product as the hydrohalide salt, and convert it into the free base in a separate step. As basic substances primarily alkali and alkaline earth hydroxides, carbonates or hydrocarbonates, furthermore aqueous ammonia can be used.

As mentioned above, the compounds of the general formula (I) are of basic character and form acid addition salts with various organic or mineral acids. Of the salts primarily the hydrochlorides, hydrobromides, sulfates, phosphates, maleates, fumarates and D-tartrates are to be mentioned.

The new acylated 2-aminothiazole derivatives of the general formula (I) are valuable therapeutics. They exert a high inhibiting effect on the gastric juice secretion, thus they can be applied for the inhibition of the gastric hypersecretion as well as for the prophylaxis or treatment of gastric ulcer. The new compounds according to the invention are completely devoid of parasympatholytic (anticholinergic) side effects, thus no anticholinergic phenomena, such as mouth thickness, mydriasis, etc., take place upon the administration of the new compounds.

The effective daily dosage of the new compounds of the general formula (I) is between 10 and 500 mg.

The effects of the new compounds exerted on the gastric acid secretion and Shay ulcer was examined according to the method of H. Shay et al. (Gastroenterology 5, 43/1945/), while their inhibition effect exerted on immobilisation and insuline ulcer was tested according to the method of Borsi et al. (Acta Pharm. Hung. 38, 151 /1968/). The mydriatic effects of the new compounds was tested according to the method of P. Pulewka (Arch. f. exp. Path. u. Pharm. 168, 306 /1932/), in order to decide whether they possess anticholinergic side effects or not. All experiments were carried out on rats. As reference substance, methantheline (diethyl-/2-hydroxyethyl/-methylammonium bromide xanthene-9-carboxylate) was used. The results of the above tests are summarized in Table 1.

Table 1

| Compound (No. of Example) | Inhibition of gastric juice secretion, $ED_{50}$ mg./kg. p.o. | Ulcer-inhibiting effect $ED_{50}$ mg./kg. p.o. | | | Anticholinergic effect, $ED_{50}$ | | Acute toxicity $LD_{50}$ mg./kg. | |
|---|---|---|---|---|---|---|---|---|
| | | Shay | immob. | insulin | ileum gamma | Pulewka mg./kg. | p.o. | i.p. |
| 2 | 8 | 40 | 27 | 6 | >1 | >100 | 420 | 310 |
| 4 | 16 | >40 | 40 | 12 | >1 | >100 | 550 | 240 |
| 5 | 40 | >40 | 40 | >40 | >1 | >100 | 1400 | 460 |
| 8 | 20 | >40 | — | — | >1 | >100 | 1000 | >1000 |
| 16 | >40 | >40 | >40 | >40 | >1 | >100 | >2000 | >1000 |
| 17 | >40 | >40 | >40 | >40 | >1 | >100 | 1300 | 650 |
| 18 | >40 | >40 | — | — | >1 | >100 | 1300 | >1000 |
| 19 | >40 | >40 | — | — | >1 | >100 | >2000 | >1000 |

Table 1-continued

| Compound (No. of Example) | Inhibition of gastric juice secretion, $ED_{50}$ mg./kg. p.o. | Ulcer-inhibiting effect $ED_{50}$ mg./kg. p.o. | | | Anticholinergic effect, $ED_{50}$ | | Acute toxicity $LD_{50}$ mg./kg. | |
|---|---|---|---|---|---|---|---|---|
| | | Shay | immob. | insulin | ileum gamma | Pulewka mg./kg. | p.o. | i.p. |
| 24 | 23 | >40 | >40 | 20 | >1 | >100 | 350 | 200 |
| 27 | 30 | 50 | 25 | 20 | >1 | >100 | 450 | 300 |
| 28 | 40 | >40 | — | — | >1 | >100 | 800 | 200 |
| 31 | 19 | 50 | 30 | 20 | >1 | >100 | 1000 | 500 |
| 32 | 35 | >40 | >40 | >40 | >1 | >100 | >1500 | 400 |
| 33 | 20 | — | — | — | >1 | >100 | 900 | 600 |
| Methantheline | 20 | 15.2 | 20.7 | 11.5 | $3\times10^{-5}$ | 17 | 320 | 76 |

The compounds of the general formula (I) on their pharmaceutically acceptable acid addition salts can be administered to humans or animals in the form of pharmaceutical compositions, such as tablets, coated tablets, pills, capsules, solutions, suspensions, injectable preparations, suppositories, etc. These pharmaceutical compositions are prepared by known methods, using the conventional pharmaceutical carriers, diluents and/or auxiliary agents. The pharmaceutical compositions can be sterilized, if required.

The invention is elucidated in detail by the aid of the following non-limiting Examples.

EXAMPLE 1

Preparation of 2-glycylamido-4-(3'-pyridyl)-thiazole

Step A: Preparation of 2-chloroacetamido-4-(3'-pyridyl)-thiazole

A solution of 13.5 ml. of chloroacetyl chloride in 48 ml. of dry dimethylformamide is added dropwise to the stirred suspension of 28.8 g. of 2-amino-4-(3'-pyridyl)-thiazole (J. Heterocyclic Chem. 7, 1139 /1970/) in 100 ml. of dry dimethylformamide and 14.5 ml. of dry pyridine. During the addition the mixture is cooled with an ice bath and the internal temperature is maintained at +3°C. When the addition is complete, the mixture is allowed to stand in refrigerator overnight, then it is admixed with 360 ml. of cold water under vigorous stirring. The separated yellow precipitate is filtered off, washed pyridine-free with ice water, and dried at room temperature. 37.75 g. (91 %) of 2-chloroacetamido-4-(3'-pyridyl)-thiazole are obtained; m.p.: 272°–276°C.

Step B: Preparation of 2-glycylamido-4-(3'-pyridyl)-thiazole 7.6 g. of 2-chloroacetamido-4-(3'-pyridyl)-thiazole are suspended in 200 ml. of dimethylformamide, and dry gaseous ammonia is introduced into the suspension at room temperature for 22 hours, under vigorous stirring. A red solution is formed. The solvent is evaporated under reduced pressure, and the residue is recrystallized from a mixture of ethanol and dimethylformamide. 5.5 g. (68%) of 2-glycylamido-4-(3'-pyridyl)-thiazole hydrochloride are obtained; m.p.: 235°–240°C.

The hydrochloride is dissolved in 100 ml. of water and the solution is rendered alkaline with 8% aqueous ammonia. 4.07 g. of 2-glycylamido-4-(3'-pyridyl)-thiazole are obtained; m.p.: 188°–194°C. After recrystallization from a mixture of dimethylformamide and ethanol, the product melts at 192°–195°C.

EXAMPLE 2

Preparation of 2-cyclopropylamino-acetamido-4-(3'-pyridyl)-thiazole 18 ml. of cyclopropylamine are added to a stirred mixture of 10.2 g. of 2-chloroacetamido-4-(3'-pyridyl)-thiazole and 120 ml. of dimethylformamide, and the mixture is heated to 55°C to obtain a clear solution. After 4 hours 50% of the solvent is evaporated under reduced pressure, and isopropanol saturated with dry hydrochloric acid is added to the residue. The separated solid is filtered off. 12.9 g. (93%) of 2-cyclopropylaminoacetamido-4-(3'-pyridyl)-thiazole dihydrochloride are obtained; m.p.: 246°–247°C (after recrystallization from a mixture of methanol and acetone).

1 g. of the thus-obtained salt is dissolved in 10 ml. of water, and the solution is rendered alkaline with 8% aqueous ammonia. The separated crystalline substance is filtered off and recrystallized from isopropanol. 0.4 g. of 2-cyclopropylamino-acetamido-4-(3'-pyridyl)-thiazole are obtained; m.p.: 189°–192°C.

EXAMPLE 3

Preparation of 2-(β-hydroxyethylamino-acetamido)-4-(3'-pyridyl)-thiazole 20 ml. of ethanolamine are added to a stirred mixture of 15.2 g. of 2-chloroacetamido-4-(3'-pyridyl)-thiazole and 80 ml. of dimethylformamide. A red solution is formed, and after several hours a crystalline substance separates from the solution. The crystalline substance is collected by filtration, and the mother liquor is concentrated to one-half volume under reduced pressure to yield a further amount of the end-product. This way a total amount of 15.5 g. (96%) of 2-(β-hydroxyethylaminoacetamido)-4-(3'-pyridyl)-thiazole is obtained; m.p.: 186°–189°C (after recrystallization from ethanol).

EXAMPLES 4 TO 29

The procedure described in Example 3 is repeated, but the following amino compounds are used as reactants: monoethylamine, diethylamine, allylamine, β-dimethylaminoethylamine, benzylamine, cyclohexylamine, 2-furylmethylamine, 3-hydroxypropylamine, 2-(1-hydroxy-2-methyl)-propylamine, 2-(1-hydroxy)-butylamine, diethanolamine, aniline, piperidine, morpholine, heptamethyleneimine, 4-methyl-piperazine, n-propylamine, isopropylamine, n-butylamine, isobutylamine, sec-butylamine, t-butylamine, n-hexylamine, n-octylamine and di-n-butylamine. The obtained products are listed in Table 2.

Table 2

| No. of Example | Product | M.p. °C |
|---|---|---|
| 4 | 2-(Ethylamino-acetamido)-4-(3'-pyridyl)-thiazole | 238–242 |
| 5 | 2-(Diethylamino-acetamido)-4-(3'-pyridyl)-thiazole | 178–182 |
| 6 | 2-(Allylamino-acetamido)-4-(3'-pyridyl)-thiazole | 242–246 |
| 7 | 2-($\beta$-Dimethylaminoethylamino-acetamido)-4-(3'-pyridyl)-thiazole trihydrochloride dihydrate | 169–172 |
| 8 | 2-(Benzylamino-acetamido)-4-(3'-pyridyl)-thiazole | 182–185 |
| 9 | 2-(Cyclohexylamino-acetamido)-4-(3'-pyridyl)-thiazole | 178–180 |
| 10 | 2-(2'-Furylmethylamino-acetamido)-4-(3''-pyridyl)-thiazole | 182–184 |
| 11 | 2-(3'-Hydroxypropylamino-acetamido)-4-(3''pyridyl)-thiazole | 186–188 |
| 12 | 2-(2'-Hydroxypropylamino-acetamido)-4-(3''-pyridyl)-thiazole | 181–183 |
| 13 | 2-(2'-/1'-Hydroxy-2'-methyl/-propyl-amino-acetamido)-4-(3''-pyridyl)-thiazole | 173–174 |
| 14 | 2-(2'-/1'-Hydroxy/-butylamino-acetamido)-4-(3''-pyridyl)-thiazole | 162–165 |
| 15 | 2-(Bis-/$\beta$-hydroxyethyl/-amino-acetamido)-4-(3'-pyridyl)-thiazole | 175–178 |
| 16 | 2-(Phenylamino-acetamido)-4-(3'-pyridyl)-thiazole | 254–256 |
| 17 | 2-(Pentamethylencimino-acetamido)-4-(3'-pyridyl)-thiazole | 166–169 |
| 18 | 2-(4'-Morpholino-acetamido)-4-(3''-pyridyl)-thiazole | 212–214 |
| 19 | 2-(Heptamethyleneimino-acetamido)-4-(3'-pyridyl)-thiazole | 191–193 |
| 20 | 2-(1'-/4'-Methyl-piperazino/-acetamido)-4-(3''-pyridyl)-thiazole | 179–181 |
| 21 | 2-(n-Propylamino-acetamido)-4-(3'-pyridyl)-thiazole dihydrochloride | 258–262 |
| 22 | 2-(Isopropylamino-acetamido)-4-(3'-pyridyl)-thiazole dihydrochloride | 265–269 |
| 23 | 2-(n-Butylamino-acetamido)-4-(3'-pyridyl)-thiazole dihydrochloride | 218–226 |
| 24 | 2-(Isobutylamino-acetamido)-4-(3'-pyridyl)-thiazole dihydrochloride | 240–245 |
| 25 | 2-(sec-Butylamino-acetamido)-4-(3'-pyridyl)-thiazole dihydrochloride | 244–249 |
| 26 | 2-(t-Butylamino-acetamido)-4-(3'-pyridyl)-thiazole dihydrochloride | 263–268 |
| 27 | 2-(n-Hexylamino-acetamido)-4-(3'-pyridyl)-thiazole dihydrochloride | 152–155 |
| 28 | 2-(n-Octylamino-acetamido)-4-(3'-pyridyl)-thiazole dihydrochloride | 242–246 |
| 29 | 2-(Di-n-butylamino-acetamido)-4-(3'-pyridyl)-thiazole | 135–137 |

EXAMPLE 30

Preparation of 2-cyclopropylamino-acetamido-4-(2'-pyridyl)-thiazole dihydrochloride

Step A: Preparation of 2-chloroacetamido-4-(2'-pyridyl)-thiazole

A solution of 13.5 ml. of chloroacetyl chloride in 48 ml. of dimethylformamide is added, within 3 hours, to a stirred suspension of 28.8 g. of 2-amino-4-(2'-pyridyl)-thiazole (German Patent No. 1,062,245) in 100 ml. of dry dimethylformamide and 14.5 ml. of pyridine. During the addition the mixture is cooled on an ice bath, thereafter it is placed into a refrigerator. Next day the solution is mixed with 400 ml. of water, the separated crystalline substance is filtered off, washed with ice water and ethanol, and dried at 50°C. 35.38 g. (87.0 %) of 2-chloracetamido-4-(2'-pyridyl)-thiazole are obtained; m.p.: 181°–184°C. This substance is used in the next step without any subsequent purification.

Step B: Preparation of 2-cyclopropylamino-acetamido-4-(2'-pyridyl)-thiazole dihydrochloride 20 ml. of cyclopropylamine are added to a stirred suspension of 24.5 g. of 2-chloroacetamido-4-(2'-pyridyl)-thiazole in 60 ml. of dry dimethylformamide. The mixture warms slightly, and the chloroacetyl compound enters into the solution. The mixture is stirred for 5 hours, and then allowed to stand overnight. Thereafter 50 ml. of the liquids are evaporated under reduced pressure, and 70 ml. of 7% isopropanolic hydrochloric acid are added to the residue. The separated crystalline salt is filtered off. 28.0 g. of 2-cyclopropylamino-acetamido-4-(2'-pyridyl)-thiazole dihydrochloride are obtained; m.p.: 185°–190°C. This crude substance is recrystallized from 90% aqueous methanol to yield 16.8 g. (48%) of a purified substance melting at 214°–218°C.

EXAMPLE 31

Preparation of 2-cyclopropylamino-acetamido-4-(3'-pyridyl)-5-methyl-thiazole dihydrochloride Step A: Preparation of 2-chloroacetamido-4-(3'-pyridyl)-5-methyl-thiazole 11.6 g. of 2-amino-4-(3'-pyridyl)-5-methyl-thiazole (m.p.: 191°–194°C; prepared by reacting 3-propionyl-pyridine with bromine and treating the obtained 3-/α-bromopropionyl/-pyridine hydrobromide with thiourea) are suspended in a mixture of 64 ml. of dry dimethylformamide and 5.5 ml. of dry pyridine, and a solution of 5.92 ml. of chloroacetyl chloride in 10 ml. of dry dimethylformamide is added to the stirred suspension within 2 hours. During the addition the mixture is cooled on an ice bath. The mixture is kept in a refrigerator overnight, then poured into 200 ml. of ice water. The separated crystals are filtered off, washed with ice water, and dried at 50°C. 10.84 g. (66.9 %) of 2-chloroacetamido-4-(3'-pyridyl)-5-methyl-thiazole are obtained; m.p.: 264°–266°C. This substance is used in the next step without purification.

Step B: Preparation of 2-cyclopropylamino-acetamido-4-(3'-pyridyl)-5-methyl-thiazole dihydrochloride 10 ml. of cyclopropylamine are added to a stirred suspension of 10.8 g. of 2-chloroacetamido-4-(3'-pyridyl)-5-methyl-thiazole in 25 ml. of dry dimethylformamide. The mixture warms slightly, and a solution forms. The solution is stirred for 4 hours, thereafter mixed with 150 ml. of cold water. An oily product separates, which solidifies on standing. The crystalline substance is filtered off, washed with water, and dried at 50°C. 10.2 g. (87.6 %) of 2-cyclopropylamino-acetamido-4-(3'-pyridyl)-5-methyl-thiazole are obtained; m.p.: 128°–134°C.

The obtained product is converted into its dihydrochloride in a methanol medium. 11.14 g. (76.5 %) of the dihydrochloride are obtained, m.p.: 224°–228°C. After recrystallization from 75% aqueous methanol, the melting point raises to 235°–238°C.

EXAMPLE 32

Preparation of 2-(2'-hydroxyethylamino-acetamido)-4-(3''-pyridyl)-5-methyl-thiazole A mixture of 8.0 g. of 2-chloroacetamido-4-(3'-pyridyl)-5-methyl-thiazole, 20 ml. of dry dimethylformamide and 12 ml. of ethanolamine is maintained at room temperature for one hour. The obtained solution is admixed with ice water, and allowed to stand in a refrigerator. Next day the separated crystals are filtered off, washed with water, and dried at 50°C., 5.2 g. (59.5 %) of 2-(2'-hydroxyethylamino-acetamido)-4-(3'λ'pyridyl)-5-methyl-thiazole are obtained; m.p.: 176°–179°C. After recrystallization from ethanol, the melting point raises to 178°–180°C.

EXAMPLE 33

Preparation of 2-cyclopropylamino-acetamido-4-(4'-pyridyl)-thiazole dihydrochloride Step A: Preparation of 2-chloroacetamido-4-(4'-pyridyl)-thiazole One proceeds as described in Step A of Example 30, but 2-amino-4-(4'-pyridyl)-thiazole (J. Heterocyclic Chem. 7, 1135 /1970/) is used as starting substance. 22.7 g. (52.4 %) of the title compound is obtained, m.p.: 284°–287°C. This product is used in the next step without purification.

Step B: Preparation of 2-cyclopropylamino-acetamido-4-(4'-pyridyl)-thiazole dihydrochloride 20 ml. of cyclopropylamine are added to a mixture of 17.1 g. of 2-chloroacetamido-4-(4'-pyridyl)-thiazole and 70 ml. of dry dimethylformamide. The mixture is stirred at room temperature for 3 hours, thereafter the excess of the amine is evaporated under reduced pressure. The residue is treated with isopropanolic hydrochloric acid to obtain 17.6 g. (72.7 %) of 2-cyclopropylamino-acetamido-4-(4'-pyridyl)-thiazole dihydrochloride; m.p.: 242°–246°C. After recrystallization from a mixture of 90% aqueous methanol and acetone, the melting point raises to 263°–267°C.

What we claim is:

1. An acylated 2-aminothiazole derivative selected from the group consisting of a compound of the formula

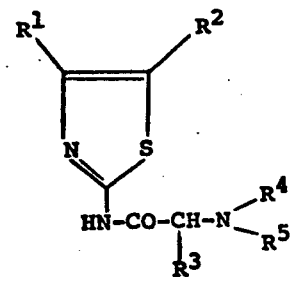

in which
R$^1$ is pyridyl,
R$^2$ is a member selected from the group consisting of hydrogen and lower alkyl,
R$^3$ is a member selected from the group consisting of hydrogen, methyl and ethyl,
R$^4$ is hydrogen,
R$^5$ is a member selected from the group consisting of hydrogen, C$_{1-8}$ alkyl, allyl, hydroxyalkyl, C$_{3-6}$ cycloalkyl, β-dimethylaminoethyl, β-diethylaminoethyl, benzyl, 2-furylmethyl, unsubstituted phenyl, phenyl substituted with a member selected from the group consisting of halogen, methyl, methoxy and trifluoromethyl, or
both R$^4$ and R$^5$ are hydroxyalkyl,
and a pharmaceutically acceptable acid addition salt thereof.

2. An acylated 2-aminothiazole derivative selected from the group consisting of a compound of the formula

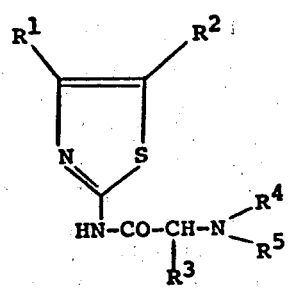
in which
R[1] is pyridyl,
R[2] is hydrogen,
R[3] is hydrogen,
R[4] is cyclopropyl,
R[5] is hydrogen,
and a pharmaceutically acceptable acid addition salt thereof.
* * * * *